US010213267B2

(12) United States Patent
King et al.

(10) Patent No.: US 10,213,267 B2
(45) Date of Patent: Feb. 26, 2019

(54) SURGICAL DRAPE WITH CONTROL MECHANISM

(75) Inventors: Brent King, DeWinton (CA); Dale McKay, Airdrie (CA)

(73) Assignee: Tenet Medical Engineering, Inc. (CA)

( * ) Notice: Subject to any disclaimer, the term of this patent is extended or adjusted under 35 U.S.C. 154(b) by 245 days.

(21) Appl. No.: 12/581,587

(22) Filed: Oct. 19, 2009

(65) Prior Publication Data

US 2011/0088702 A1  Apr. 21, 2011

(51) Int. Cl.
*A61B 46/00* (2016.01)
*A61B 46/10* (2016.01)
*A61B 46/20* (2016.01)
*A61B 46/23* (2016.01)

(52) U.S. Cl.
CPC .............. *A61B 46/10* (2016.02); *A61B 46/20* (2016.02); *A61B 46/23* (2016.02); *A61B 46/30* (2016.02); *A61B 46/40* (2016.02)

(58) Field of Classification Search
CPC ....... A61B 19/00; A61B 19/02; A61B 19/029; A61B 19/08; A61B 19/081; A61B 46/00; A61B 46/10; A61B 46/13; A61B 46/20; A61B 46/30; A61B 46/40; A61F 2013/15073; A61M 1/0088
USPC .................. 128/849, 850, 851, 852, 200.26; 600/437; 206/440
See application file for complete search history.

(56) References Cited

U.S. PATENT DOCUMENTS

| 5,178,162 A * | 1/1993 | Bose .................. A61B 46/27 128/849 |
| 5,648,821 A * | 7/1997 | Becker ................ A61B 46/10 345/161 |
| 6,371,121 B1 | 4/2002 | Faries, Jr. et al. |
| 6,471,172 B1 * | 10/2002 | Lemke ................ A61B 90/50 248/125.7 |
| 7,096,870 B2 * | 8/2006 | Lamprich ........... A61B 46/23 128/849 |
| 7,438,705 B2 * | 10/2008 | Karpowicz ........ A61M 1/0001 604/313 |
| 2007/0295341 A1 * | 12/2007 | Scott .................. A61B 46/10 128/849 |

* cited by examiner

*Primary Examiner* — Ophelia A Hawthorne
*Assistant Examiner* — Caitlin A Carreiro
(74) *Attorney, Agent, or Firm* — Burns & Levinson, LLP; Joseph M. Maraia

(57) ABSTRACT

A disposable sterile surgical drape configured for establishing a sterile field around a surgical instrument such as a limb positioner includes a control mechanism associated with the drape in the sterile field that interfaces with, and controls, the surgical instrument. The control mechanism includes a switch and a communication interface that connects to the instrument and the location of the switch may be moved to a desired position within the sterile field.

29 Claims, 3 Drawing Sheets

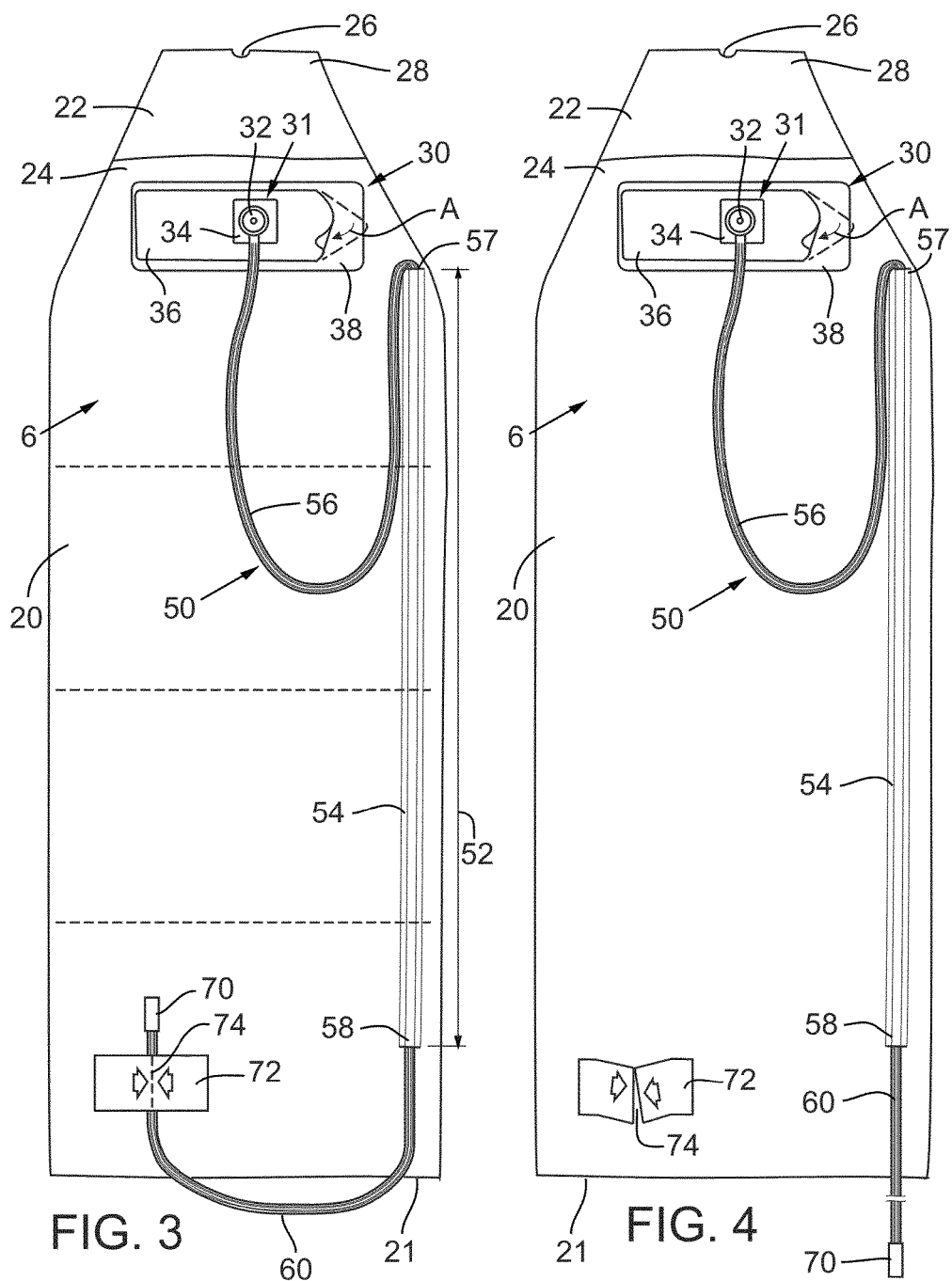

SURGICAL DRAPE WITH CONTROL MECHANISM

FIELD OF THE INVENTION

The present invention relates to disposable sterile surgical drapes and more particularly to a surgical drape that incorporates a control mechanism that allows a surgeon or other worker to control the position of equipment associated with the surgical drape.

BACKGROUND INFORMATION

During surgical procedures there is a need to maintain a sterile field around the surgical wound site. A surgical drape is a tool that helps to create and maintain the sterile surgical field by creating a physical barrier between the sterile field and the non-sterile field that minimizes the passage of microorganisms between the sterile field and non-sterile areas outside of the field. Maintaining sterility in the surgical field typically requires that instruments that are used in the field are sterilized before they are introduced into the field. However, some devices that are used during surgical procedures are not easily sterilized; such devices are therefore draped or covered with sterile protective covers—surgical drapes. Often these covers are disposable.

An example of a device used during surgery that does not lend itself to sterilization is a limb positioning tool. These devices help the surgical team position a patient's limb during surgery but given their bulkiness cannot be easily sterilized using standard sterilization equipment and techniques. For example, during many orthopedic surgical procedures such as shoulder surgery the patient's arm and shoulder must be positioned and repositioned to provide the surgical team with adequate access to the surgical site. Limb positioning devices make the job of limb positioning and adjustment relatively easy. However, the positioning devices can be bulky, and hence surgical drapes are used to cover the limb positioner and isolate the sterile wound site from the equipment.

There are numerous types of positioning tools and most are adapted to be connected to or closely associated with an operating room table. An electrically operated positioning tool has an extension that attaches to and which supports a patient's limb or other portion of the patient either directly or with an accessory specifically designed to engage the patient. The electrical positioning tool allows the surgical staff to manipulate and orientate both the patient's limb and surgical implements during the procedure in what are known as interpretive movements. Often during surgical procedures the surgical staff will perform numerous interpretive movements. In order for the draped positioning device to perform its function, some form of communication is required from the surgeon or other member of the surgical team, who is in the sterile surgical field, to the positioning device, which is outside of the sterile field by virtue of the drape isolating the device. This communication between surgical staff and the positioning device often involves the use of switches, levers, knobs and buttons of various descriptions—all of which are referred to herein for ease of reference as "control surfaces." These control surfaces are located outside of the sterile field and must be accessed and manipulated through the drape material. In other words, a member of the surgical team must actuate the control surface with the surgical drape positioned between the team member's hand and the control surface in order to maintain the sterile field. Activating control surfaces such as switches, levers and knobs can be quite difficult when performed through a sterile drape.

In addition, the risk of tearing the surgical drape and compromising the sterile field increases with repeated access to the control surface. Thus, as the surgical team performs more interpretive movements, there is a risk of tearing the surgical drape. Moreover, because the surgical drape necessarily defines a barrier between the surgical team and the control surface, that barrier that can obstruct the appearance and feel of the control surface. This can result in an unintentional movement of the positioning device that may compromise the surgical procedure.

Some positioning equipment, particularly electrically operated equipment, has control surfaces that are located in positions that are remote from the operative end of the equipment that engages the patient and thus do not interfere with the range of motion of the device. These kinds of equipment may be activated without the team member accessing the control surface through the drape. For example, some equipment have control surfaces such as foot pedals that when depressed activate the positioner, which allow a full range of motion during set up of the equipment and prevent entanglement or wind up of associated wires or tubes that are needed to communicated between the control surface and the positioning equipment. However, a remotely located control surface such as a foot pedal is not ideal for the surgical team because it requires manipulation from a position that is removed from the surgical site and necessarily requires that the team member's attention is directed elsewhere, away from the surgical site to the remote actuator. This is a distraction that can cause problems during the surgical procedure, and at a minimum is an unnecessary distraction.

There are distinct advantages to having the ability to locate the control surface for a positioning device to a position that is convenient to the surgeon. The location could be on the patient, a secondary drape, a piece of related equipment or near such equipment, or anywhere within the surgical field that is convenient. Because there are a variety of different kinds of positioning equipment and because some positioning equipment may be used for multiple positioning challenges, the ideal location for a control surface would be changeable from procedure to procedure, application to application, as well as to satisfy the preference of each surgeon. Thus, the optimal location of a control surface is variable within the surgical field and depends upon the particular equipment being controlled, the procedure being performed and the particular surgeon's preference.

Accordingly, there is a need for a sterile barrier adapted to incorporate a mechanism for controlling surgical equipment that addresses these and other concerns.

The present invention defines a surgical drape with a control surface integrated therein that meets these and other needs. The invention provides an improved sterile disposable drape incorporating a control mechanism that is in the sterile field and that allows for actuation and greater control of positioning equipment, overcoming many of the deficiencies of known devices. A disposable sterile drape according to the present invention has an integrated sterile control surface located on an outer surface of the drape to protect against compromising the sterile field. The entire drape, including the integrated control surface is disposable. By positioning the control surface on an outer surface of the drape, risk that damage to the drape will occur during surgical interpretive movements, with associated compromise of the sterile barrier is greatly reduced in comparison to the situation where the control surface must be manipulated through the drape. The location of the control surface on the outside of the drape reduces the chance of accidental or undesired activation of the positioning device that is activated by the control surface due to confusion caused by the drape obstructing the surgeon's view of the control surfaces beneath the drape. With the control surface mounted in plain view on the sterile side of the drape, the control mechanisms are easily visible and easily activated, preventing undesired activation.

The invention defines a disposable sterile drape having an integrated sterile disposable control surface on the outside of the drape that locates the control surface for improved tactile feel of the user. The location of the control surface can be changed within the sterile field so that the surgeon may select a position for the control surface that is advantageous for a particular piece of electrical positioning equipment or which otherwise satisfies the surgeon. The positioning of the control surface may be improved by moving it to a location closer to the operative end of the equipment that is activated by the control surface. Once the positioning device is set up for a surgical procedure and the need for large range patient motions have been completed, the drape and the control surface may be used to cover the positioning device to establish a sterile field around the device. Moreover, once set up is performed, the range of motion of the positioning equipment is typically limited; the control surface located on an outer surface of the drape provides for sufficient mobility to allow all needed motion while placing the activation mechanism in a desired location.

The present invention defines a disposable sterile drape having an integrated sterile disposable control surface on an outer surface of the drape that can be relocated within the sterile field to an area other than the drape, such as a patient surface, secondary drape or accessory equipment. The control surface defines apparatus for controlling positioning equipment and it may be removed from its location on the outer surface of the drape and placed through the use of an adhesive or another attachment means to a location anywhere within the sterile field, limited only by the length or the range of transmission of the communication interface element that extends from the activation element.

The disposable sterile drape according to the invention may be used with numerous different types of positioning equipment used in surgical procedures, including for example limb positioners and operating room tables. The invention may further be used with surgical tools such as various scoping instruments, retractors and the like.

These and other advantages of the invention described herein and defined by the appended claims will be evident from review of the following description and drawings.

BRIEF DESCRIPTION OF THE DRAWINGS

The invention will be better understood and its numerous objects and advantages will be apparent by reference to the following detailed description of the invention when taken in conjunction with the following drawings.

FIG. 3 is a plan view of a disposable surgical drape according to the present invention incorporating an integral control surface, and illustrating the drape in an extended or unfolded position, ready for use.

FIG. 4 is a plan view of a disposable surgical drape shown in FIG. 3, illustrating the electrical conductive element removed from its attachment to the drape and ready to be connected to the positioning equipment.

DETAILED DESCRIPTION OF ILLUSTRATED EMBODIMENTS

Figure 1:
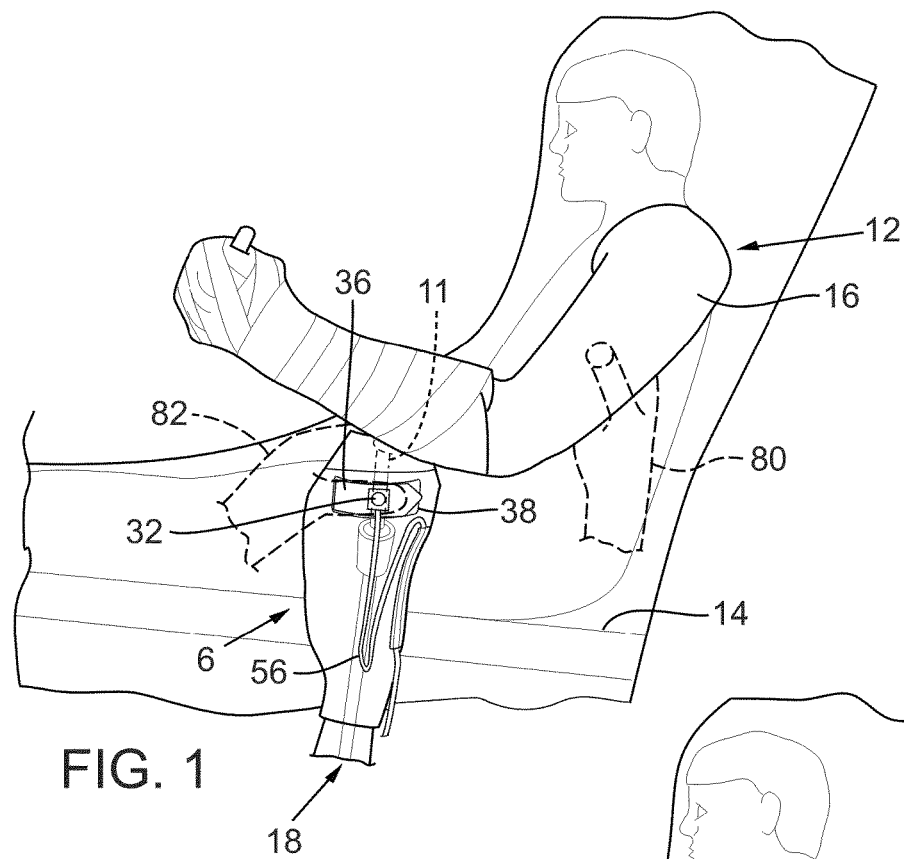
FIG. 1 is a side elevation view showing a disposable surgical drape incorporating an integral control surface according to the present invention, illustrating the surgical drape positioned on an electrical positioning device, and more particularly a limb positioning device that is supporting a patient's arm, where the integral control surface is attached to an outer surface of the drape.
Figure 2:
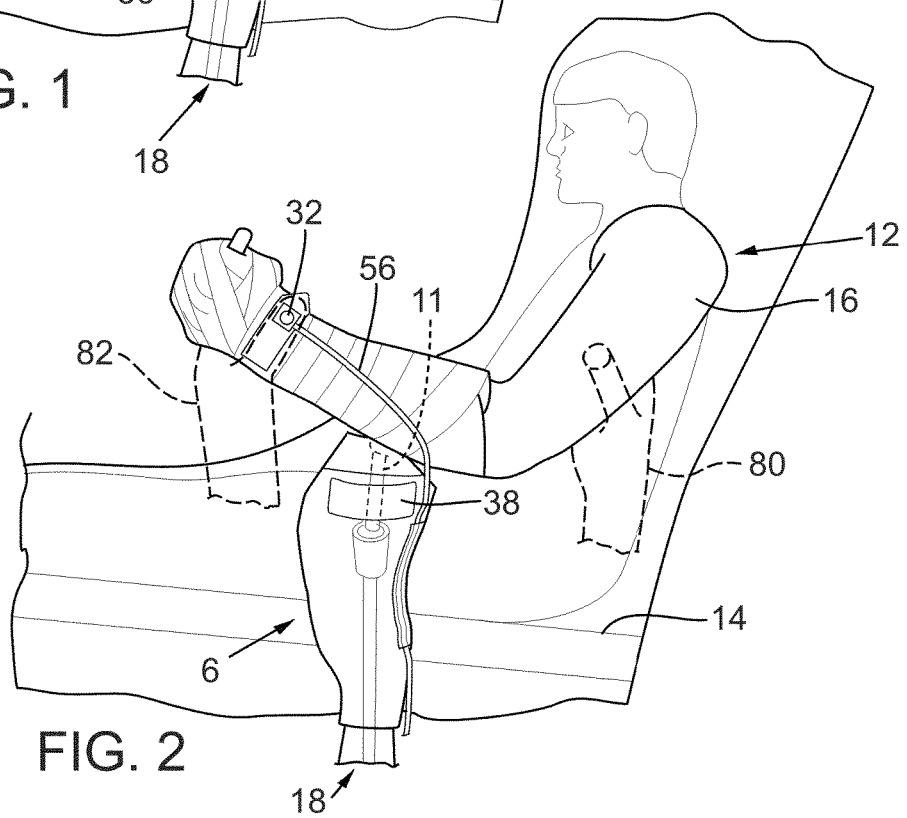
FIG. 2 is a side elevation view similar to FIG. 1 but showing the control surface repositioned relative to the position of the control surface of FIG. 1 and such that the control surface has been adhered to the patient's wrist.

A first illustrated embodiment of a disposable surgical drape 6 that incorporates an integrally and pre-attached disposable control mechanism, referred to herein as control surface 30 according to the present invention is illustrated in FIGS. 1 through 5. In FIGS. 1 and 2 the control surface 30 is shown as used in a surgical situation with a patient 12, in order to provide context. Thus, in FIG. 1 a patient 12 is shown sitting on an operating room table 14 and the patient's left arm 16 is illustrated being supported by a limb positioning apparatus 18, typical of the manner in which a patient's arm would be positioned for orthopedic surgery on the patient's shoulder.

There are numerous different kinds of limb positioning devices and other surgical equipment on the market with which the present invention may be utilized and the invention is not limited in any way to use with any particular kind of positioning device or other surgical equipment, but instead may be used with any instrument used during surgical procedures. An exemplary limb positioning apparatus 18 is manufactured by Tenet Medical Engineering (tenetmedical.com) and is sold under the trademark SPIDER®. The present invention may similarly be used with utilized with positioning devices such as operating room tables. Most surgical tables include controls that are operable to control the position various parts of the table. Often, these controls are located on a pendant or other similar activation module that is located outside of the sterile field. The present invention may be used to define a control surface for the operating room table that allows the table to be controlled from within the sterile field. Other instruments with which the invention may be used include scopes of various descriptions and tools such as retractors and these instruments may be utilized in combination with devices such as a limb positioner. Thus, the invention contemplates a sterile drape for a limb positioner that is attached to a secondary surgical instrument such as a scope or retractor. All such equipment with which the present invention may be utilized is referred to herein as instruments or surgical instruments.

At times herein, positional relationships between various structures are described with relative directional terms. The ground plane on which operating room table 14 sits is used as the primary reference point for a naming convention for such terms. Thus, the word "upper" or "upwardly" refers to the direction above and away from the ground plane and the word "lower" or "downwardly" refers to the direction toward the ground plane. Other relative directional terms correspond to this convention: the direction toward the "rear" of the patient is the direction toward the patient's back as the patient is oriented on operating room table 14 and the opposite direction, or "forward", is the direction toward the patient's feet.

With reference now to FIG. 3, disposable surgical drape 6 comprises an elongate tubular main body portion 20 and an attached rubber dam portion 22 at a distal end 24 of the main body portion 20. The proximate end, or open end 21 of the tubular main body portion is open. The tubular main body portion 20 may be fabricated from a variety of different materials that may be sterilized and which are preferably latex-free, such as polyethylene plastics. The tubular main body portion 20 may be formed from a pre-formed tubular sheet of the plastic material, as shown herein, or from plural sheets of plastic material formed into a tube with longitudinal seams.

The dam portion 22 at distal end 24 is attached to the main body portion 20 in an appropriate manner such as sonic welding or adhesives, and like the main body portion, may be fabricated from any number of materials. One preferred material is a rubber product sold under the trademark KARTON®. An opening 26 at the distal end 28 of dam portion 22 allows an operative arm 11 of the limb positioning device 18 to extend through the opening in the dam portion and provide support for or engagement of the patient's arm 16 (see FIG. 1)—the distal end 28 of the dam portion 22 is otherwise closed. It will be appreciated that the dimensions and configuration of the surgical drape 6 will vary depending upon the type and structure of the positioning device or other equipment that the drape is designed to cover. The drape 6 illustrated herein is exemplary only. As just one example of the other types of drapes which the invention may be used, some surgical drapes are sealed at one end so that the positioning device is completely covered by and contained within the sterile drape. There are numerous other examples and it is to be understood that the present invention is not limited to use with any particular style or type of drape.

The control surface 30 is an integral component of the drape 6 and is pre-attached to the drape. The control surface 30 is defined by several components, including in the preferred embodiment an activation element 31, which as detailed below may itself comprise several components. An electrical conduit 50 is electrically connected to activation element 31 and includes an electrical connector 70 at a distal end thereof. Each component of the control surface 30 must be capable of sterilization using conventional sterilization methodologies, and will be described separately herein. Activation element 31 comprises at least an electrical switch 32. The switch 32 may be incorporated into a backing member 34. Backing member 34 optionally has an adhesive coating on the rear side of the member, which allows the backing member and incorporated switch to be adhesively and removably attached to a secondary backing member 36, which itself is adhesively and removably attached to either the drape 6, or to a release sheet 38 that is affixed to the drape 6, as shown in FIG. 3. As illustrated with arrow A in FIGS. 3 and 4, secondary backing member 36 may be removed from release sheet 38 by pulling the secondary backing member away from the release sheet to separate the two parts. This allows the secondary backing member and the switch 32 to be repositioned to a desired location in the sterile field, as detailed below. There are numerous other means other than adhesive for detaching the switch from its original position on the drape and relocating it to another position in the sterile field and attaching it to some other surface. For example, hook and loop fabric fasteners and mechanical attachments work well in some settings.

Switch 32 is preferably a membrane-type switch that is capable of sterilization and appropriate for use in a surgical application. Electrical conduit 50 is a conventional ribbon cable that is electrically connected to switch 32 and which is readily and easily folded and manipulated. As shown in FIG. 3, electrical conduit 50 extends along the length of drape 6 from its point of connection at switch 32 to its distal, terminal end at electrical connector 70. The conduit 50 is affixed to drape 6 along an intermediate length of the conduit identified herein as an affixed length 52. As illustrated herein, the conduit 50 is affixed to main body 20 with a length of adhesive tape 54 placed over the conduit, wherein the length of adhesive tape 54 defines the affixed length 52. Alternative methods of attaching conduit 50 to main body 20 include an adhesive layer on surface of the conduit itself, or by laminating the conduit between two layers of the drape material in the case where the drape is formed of plural layers laminated together. A section 56 of conduit 50 between switch 32 and the distal end of affixed length 52 (identified with reference number 57) is free from any attachment to the drape. This allows the switch to be removed from its attachment to the drape (as described below) and repositioned to another location. Similarly, a section of the conduit (identified with reference number 56) between the proximate end 58 of affixed length 52 and electrical connector 70 is free from any attachment to the drape 6. This allows the electrical connector to be plugged into an electrical receptacle on the positioning device.

Electrical connector 70 is of the appropriate type for plugging into a receptacle on the positioning device or other equipment that is connected to and activated by switch 32, which is not shown in FIG. 3. The connector 70 is retained in place on drape 6 when the connector is not attached to the positioning device with a length of tape 72 that is perforated at dashed line 74 so that the connector 70 may be easily removed from drape 60 so that it may be plugged in. FIG. 4 illustrates removal of connector 70 from its temporary attachment to drape 6 with tape 72—the tape is separated along the perforations at line 74, which allows the connector 70 and the free section 60 of conduit 50 to be removed so that the connector may be plugged in.

With returning reference to FIGS. 1 and 2, application and operation of the control surface 30 will be described. Once patient 12 has been positioned on operating room table 14, the limb positioning device 18 is oriented adjacent the table 14 and covered with the drape 6. Specifically, open end 21 of drape 6 is slid over the positioning device and the connecting operative arm 11 of the positioning device is passed through opening 26 of dam 22. The patient's limb—in this case the patient's left arm 16—is engaged in the appropriate manner to the operative arm 11. Electrical connector 70 is removed from its attachment to drape 6 (as detailed above) and is plugged into the appropriate electrical receptacle on the positioning device (or its drive motor system). In FIGS. 1 and 2 a surgeon's right and left hands are shown in dashed lines—the surgeon's right hand is identified with reference number 80 and the left hand is given number 82. In FIG. 1, the control surface is in the same position on drape 6 as is shown in FIGS. 3 and 4. With the control surface in this position, the surgeon may activate switch 32 with the thumb of her left hand 82. When switch 32 is activated, the limb positioner 18 is activated, which allows the surgeon to manipulate the position of the patient's left arm with the surgeon's right hand 80.

In FIG. 2, the switch 32 has been removed from drape 6 by removing secondary backing member 36 and attaching the secondary backing member to the patient's left arm near the patient's wrist. As noted previously, the secondary backing member 36 has an adhesive coating on the back side thereof, which allows the secondary backing member (and the attached switch 32) to be easily attached to the patient's arm (and whatever bandages are covering the arm). As with FIG. 1, the surgeon may activate switch 32 with the thumb of her left hand, which allows for manipulation of the patient's arm with her right hand. It will be appreciated that the length of section 56 of conduit 50 may be varied to allow positioning of secondary backing member 36 and switch 32 at any desired location.

In both cases, where control surface 30 is attached to drape 6 (as in FIG. 3), or where the activation apparatus has been moved to the patient's left arm (as in FIG. 2), the activation apparatus remains in the sterile field. As noted previously, backing member 34 may also optionally be adhesively attached to secondary backing member 36. This allows for repositioning of the switch 32 and backing member 34 without secondary backing member 36.

Based on the foregoing description it will be appreciated that control surface 30, as that term is used herein, may take on several different forms and that the common function of each form is to provide an interface for controlling the positioning device from a point in the sterile field. In its most elemental form, control surface 30 is defined by an activation apparatus, most simply, a switch 32. The control surface 30 may further include a switch 32 with means for relocating the switch from an attachment to the drape to another point within the sterile field, and this means may be various forms of adhesive backings or any other suitable manner of attaching the switch to another location.

It will be understood that the conduit 50 incorporates electrical wiring that carries control signals from switch 32 to the connected positioning device. The switch 32 illustrated herein is a simple on-off circuit, but other types of switches and control devices may be used as necessary. The switch thus defines an activation device that sends signals to the appropriate part of the instrument that the drape 6 is covering. Where the instrument is a limb positioning device 18, the conduits 50 define the interface for communication between the activation device (switch 32) and the limb positioning device. It will further be appreciated that there are numerous equivalent communication interfaces that may be substituted for switch 32 and conduit 50 and which provide the same functionality of enabling a member of a surgical team to send a signal from an activator unit to a remote piece of equipment. To name just a few examples, the switch 32 may be defined by a radio frequency transmitter, or an electromagnetic or infrared sending unit, in which cases the associated equipment that is activated by the switch would be equipped with an appropriate receiver. The present invention further contemplates mechanical and electromechanical communication interfaces between the user-activated module (i.e., the switch 32) and the associated positioning device (or other device with which the drape is utilized). As one example, the switch 32 may be a button that activates a piezoelectric switch or sending unit that transmits vibration down a rod that has a piezoelectric receiver at the opposite end that transmits the control signals to the associated equipment. It will be appreciated that when the switch 32 is defined by an RF or similar wireless transmitter, or in the case of a mechanical connection, any problems associated with wind up of wires and the like are eliminated.

Figure 5:
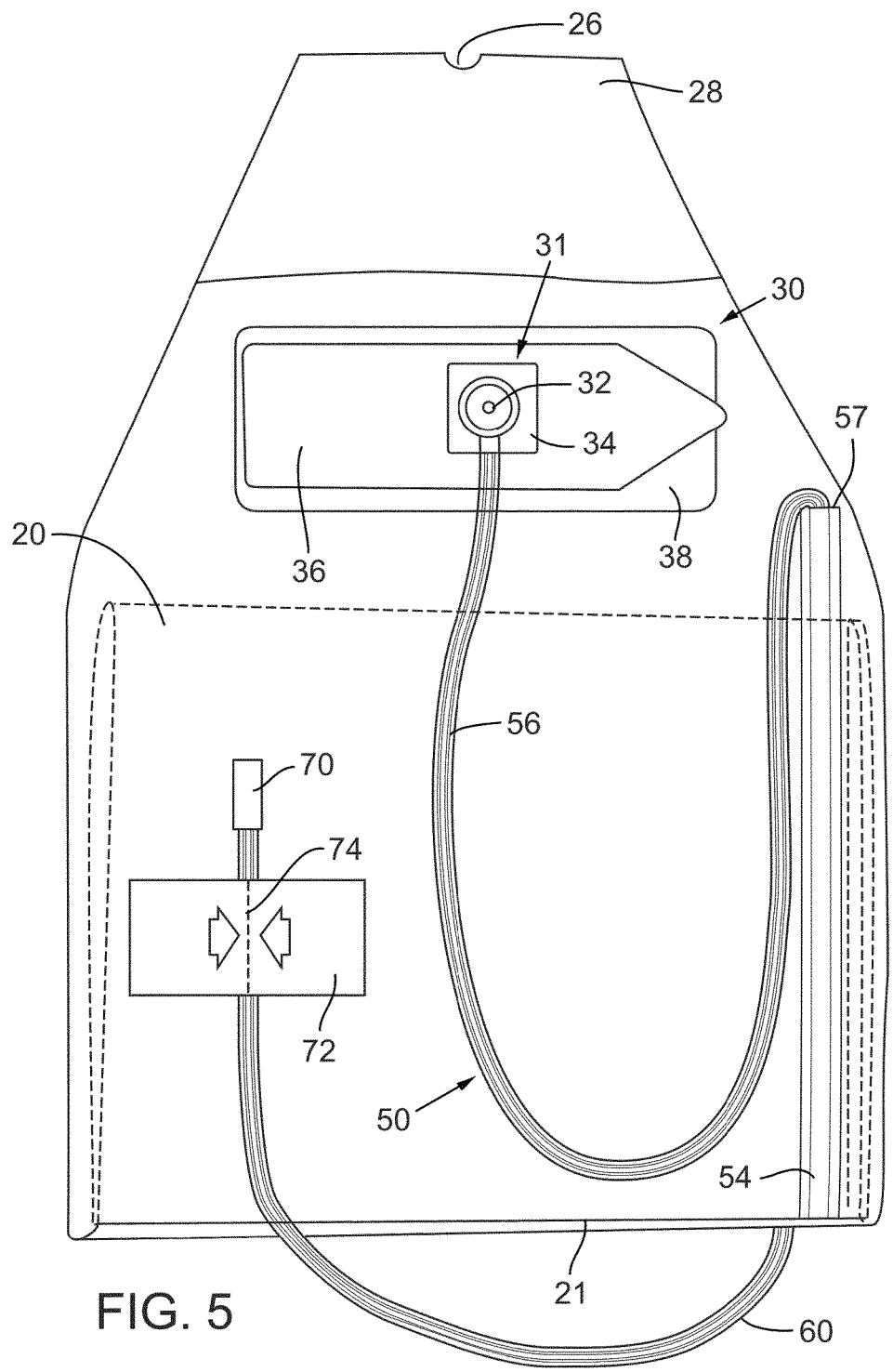
FIG. 5 is a plan view of a disposable surgical drape according to the present invention incorporating an integral control surface, illustrating the drape in a folded, storage position.

Turning now to FIG. 5, a drape 6 incorporating a control surface 30 according to the present invention is illustrated in a folded position that would be typical for storage of the drape in a sterile container prior to use. The main body of drape 6 is folded over itself along its length in order to make a more compact storage package—the flexibility of the conduit 50 allows the main body 20 to be doubled back as shown.

The control surface 30 illustrated in the attached drawings and described herein is defined by an electrical switch and associated components that carry signals from the switch to connected apparatus such as a limb positioner. However, it will be appreciated that the principles of the invention extend beyond and are not limited to an electrical switch and associated components, but instead include functional and structural equivalents of such a switch. As noted previously, as used herein the term "control surface" refers to a mechanism in the sterile field that is operable to activate a positioning device or other apparatus that is used in surgical procedures. Such an activation mechanism may take many different forms, including a variety of different types of switches, levers, knobs, buttons and the like. Similarly, the equipment that is activated by the activation mechanism may be any kind of device that is located outside of the sterile filed but, by virtue of the activation mechanism being located in the sterile field, is activated from within the sterile field. And as noted, the communication interface between the switch and the device that is activated by the switch may take many forms. Furthermore, in some instances it may be advantageous to attach the control surface 30 on the interior surface of the drape 6. In this case, the switch 32 is located outside of the sterile field. However, the switch may be activated from within the sterile field by the surgical team member pressing on the drape material to press the switch 32 against a bulkhead of some type to activate the switch.

While the present invention has been described in terms of a preferred embodiment, it will be appreciated by one of ordinary skill that the spirit and scope of the invention is not limited to those embodiments, but extend to the various modifications and equivalents as defined in the appended claims.

The invention claimed is:

1. A surgical drape for covering a surgical instrument used during surgery to define a barrier for creating a sterile field, said surgical drape comprising:

a tubular main body having an open proximal end, a distal end, and a longitudinal axis extending between the proximal and distal ends, the main body configured for passage of a surgical instrument through the open proximal end along the longitudinal axis of the main body, an outer surface of the main body being in the sterile field;

a dam portion attached to the distal end of the main body, the dam portion comprising a material selected to be different than a material of the main body;

a control surface releasably attached to the outer surface of the main body between the proximal and distal ends on a sterile side of the barrier within the sterile field, said control surface including an activation member comprising an electrical switch for completing an electrical connection on a sterile side of activation within the sterile field and performing control of the surgical instrument, the activation member performing an electrical activation responsive to a mechanical activation of the activation member, the mechanical activation and the electrical activation occurring on the sterile side of the barrier; and a communication interface that provides an electronic communication link across the sterile barrier from the activation member to the surgical instrument;

wherein the electrical switch is attached to a backing sheet that is releasably attached to a release sheet on the outer surface of the main body, and wherein the backing sheet may be removed from the release sheet and releasably attached to another surface in the sterile field; and wherein an opening formed at a distal terminus of the dam portion along the longitudinal axis is configured to permit passage therethrough of an operative arm of the surgical instrument for engaging a patient's limb or other surgical instrument.

2. The surgical drape according to claim 1 wherein the communication interface is defined by an electrical conduit electrically connected to the electrical switch and interconnecting the surgical instrument to the electrical switch.

3. The surgical drape according to claim 2 wherein the electrical conduit is attached to the outer surface of the main body along a predetermined length of the conduit.

4. The surgical drape according to claim 3 wherein the electrical conduit includes a free length of conduit that is not attached to the outer surface of the main body between the switch and the predetermined length of the conduit that is attached to the outer surface of the main body.

5. The surgical drape according to claim 4 wherein the electrical conduit includes an electrical connector at an end of the conduit opposite said switch, and where the electrical conduit includes a free length of conduit that is not attached to the outer surface of the main body between said electrical connector and said predetermined length of conduit that is attached to the outer surface of the main body.

6. The surgical drape according to claim 4 in which the free length of conduit is defined by a length of electrical conduit attaching the switch to a surface remote from the outer surface of the main body and in the sterile field.

7. The surgical drape according to claim 1 in which the surgical instrument is defined by a positioning device.

8. A surgical drape configured for covering a surgical instrument that may be operated with an activation mechanism located remotely from said surgical instrument, the surgical drape adapted for establishing a sterile field in which the surgical instrument is outside of the sterile field, the surgical drape comprising:

a tubular main body having an open proximal end, a distal end, and a longitudinal axis extending between the proximal and distal ends, the main body configured for passage of a surgical instrument through the open proximal end along the longitudinal axis of the main body, the main body having an outer surface within the sterile field;

a dam portion attached to the distal end of the main body, the dam portion comprising a material selected to be different than a material of the main body;

an activation mechanism comprising an electrical switch releasably attached to the outer surface of the main body between the proximal and distal ends and within the sterile field for completing an electrical connection on the sterile side for electrical activation within the sterile field, the activation mechanism including an electrical activation responsive to a mechanical activation of the activation member, the mechanical activation and the electrical activation occurring within the sterile field; and a communication interface interconnecting the activation mechanism across the sterile field to the surgical instrument;

wherein the electrical switch is attached to a backing sheet that is releasably attached to a release sheet on the outer surface of the main body, and wherein the backing sheet may be removed from the release sheet and releasably attached to another surface in the sterile field; and wherein an opening formed at a distal terminus of the dam portion along the longitudinal axis is configured to permit passage therethrough of an operative arm of the surgical instrument for engaging a patient's limb or other surgical instrument.

9. The surgical drape according to claim 8 wherein the surgical instrument is defined by an electrically operated positioning device.

10. The surgical drape according to claim 9, wherein the communication interface is defined by an elongate electrical conduit that is attached to the outer surface of the main body along a predetermined length of the elongate electrical conduit and wherein the elongate electrical conduit includes a free length of conduit that is not attached to the outer surface of the main body between the electrical switch and the predetermined length of the elongate electrical conduit that is attached to the outer surface of the main body; and wherein the elongate electrical conduit includes an electrical interface at a terminal end of the elongate electrical conduit, and the elongate electrical conduit includes a free length of conduit that is not attached to the outer surface of the main body between said communication interface and said predetermined length of conduit that is attached to the outer surface of the main body.

11. The surgical drape according to claim 8 wherein the surgical instrument is defined by a positioning device and in which the activation mechanism is defined by a radio frequency transmitter.

12. A method of activating a surgical instrument from a point within a sterile field during a surgical procedure, wherein the surgical instrument is located outside of the sterile field, comprising the steps of:

a) providing a surgical drape including a tubular main body having an open proximal end, a distal end, and a longitudinal axis extending between the proximal and distal ends, the main body configured for passage of a surgical instrument through the open proximal end along the longitudinal axis of the main body, a dam portion attached to the distal end of the main body, the dam portion comprising a material selected to be different than a material of the main body, and a control mechanism attached to an outer surface of the main body between the proximal and distal ends, the control mechanism comprising an electrical switch completing an electrical connection on the sterile side for activating the surgical instrument and including a communication interface for interfacing with the surgical instrument;

b) covering the surgical instrument with the surgical drape to define the sterile field externally to the surgical drape;

c) enabling the communication interface so that the communication interface is capable of sending electrical control signals across a sterile barrier defined by the surgical drape to the surgical instrument; and d) activating, on a sterile side of the surgical drape within the sterile field, the control mechanism to activate the surgical instrument, the activation performing an electrical activation responsive to a mechanical activation of the control mechanism, the mechanical activation and the electrical activation occurring on the sterile side of the barrier, wherein the electrical switch is attached to a backing sheet that is releasably attached to a release sheet on the outer surface of the main body and wherein the backing sheet may be removed from the release sheet and releasably attached to another surface in the sterile field; and wherein an opening formed at a distal terminus of the dam portion along the longitudinal axis is configured to permit passage therethrough of an operative arm of the surgical instrument for engaging a patient's limb or other surgical instrument.

13. The method according to claim 12 wherein the surgical instrument is defined by a limb positioning device, and including the steps of engaging a the patient's limb or other surgical instrument with the operative arm of the limb positioning device and manipulating a position of the patient's limb or other surgical instrument after activating the control mechanism.

14. The method according to claim 13 including the step of removing the control mechanism from being attached to the outer surface of the main body and repositioning the control mechanism to another surface within the sterile field, wherein the step of repositioning the control mechanism to another surface within the sterile field includes attaching the control mechanism to a surface other than the outer surface of the main body.

15. The surgical drape according to claim 1, wherein the control surface, including the activation member, is repositionable to a different location on the outer surface of the main body and the control surface is also repositionable to a location separated from the surgical drape.

16. The surgical drape according to claim 1, wherein the dam portion is configured to remain closed when not permitting passage therethrough of the operative arm of the surgical instrument.

17. The surgical drape of claim 16, wherein the activation member includes a radio frequency transmitter configured to transmit control signals to the surgical positioning device.

18. The surgical drape of claim 16:
wherein the communication interface includes an electrical conduit interconnecting the surgical positioning device to the electrical switch; and
wherein the electrical conduit includes a free length of conduit that is not attached to the outer surface of the main body between the electrical switch and a predetermined length of the conduit that is attached to the outer surface of the main body, the free length of conduit permitting repositioning the control surface to a location remote from the surgical drape.

19. The surgical drape of claim 1 wherein the activation member is configured to generate an activation signal on a sterile side of the barrier within the sterile field.

20. The surgical drape of claim 19 wherein the activation signal is an electrical signal generated on the sterile side of the barrier.

21. The surgical drape of claim 19 wherein the electrical switch is responsive to pressure for closing electrical contacts on the sterile side of the barrier.

22. The surgical drape of claim 1 wherein the electrical switch provides direct electrical control of surgical equipment by disposing an electrical actuator on a sterile side of the surgical drape defining the sterile field.

23. The method of claim 12 further comprising providing direct electrical control of surgical equipment by disposing an electrical actuator on a sterile side of the surgical drape defining the sterile field.

24. The method of claim 12 further comprising actuating the electrical switch and completing an electrical connection defined by contacts of the switch on the sterile side of the barrier.

25. The surgical drape of claim 8 wherein the electrical switch disposed on the sterile side is responsive to mechanical actuation of a conductive circuit element on the sterile side for manipulating an electrical connection from movement of the conductive circuit element to generate a signal on the sterile side, the signal transmitted along the communication interface for receipt by the surgical instrument.

26. The surgical drape of claim 25 further comprising an electrical coupling from the electrical switch passing outside the sterile barrier for conveying the activation, the electrical switch, a mechanical coupling and the electrical coupling integrated with the surgical drape for usage and disposal as a single-use item.

27. The surgical drape of claim 1 wherein no portion of the control surface is disposed inside of the main body.

28. The method of claim 12 wherein no portion of the control surface is disposed inside of the main body.

29. The surgical drape of claim 1 wherein the material of the dam portion is rubber.

* * * * *